United States Patent [19]
Adams

[11] Patent Number: 5,961,490
[45] Date of Patent: Oct. 5, 1999

[54] BALLOON PERFUSION CATHETER

[75] Inventor: Daniel O. Adams, Orono, Minn.

[73] Assignee: SciMed Life Systems, Inc., Maple Grove, Minn.

[21] Appl. No.: 09/013,458

[22] Filed: Jan. 26, 1998

Related U.S. Application Data

[63] Continuation of application No. 08/636,246, Apr. 23, 1996, Pat. No. 5,720,723, which is a continuation of application No. 08/520,755, Aug. 29, 1995, Pat. No. 5,556,382.

[51] Int. Cl.$^6$ .................................................. A61M 29/00
[52] U.S. Cl. ............................................. 604/96; 606/194
[58] Field of Search ................................. 604/96, 97, 98, 604/101, 102, 280; 606/191, 192, 194

[56] References Cited

U.S. PATENT DOCUMENTS

| | | | |
|---|---|---|---|
| 3,585,983 | 6/1971 | Kastrowitz et al. | 128/1 |
| 3,834,394 | 9/1974 | Hunter et al. | 128/325 |
| 4,141,364 | 2/1979 | Schultze | 128/349 |
| 4,195,637 | 4/1980 | Grüntzig et al. | 128/348 |
| 4,276,874 | 7/1981 | Wolvek et al. | 128/1 |
| 4,362,150 | 12/1982 | Lombardi, Jr. et al. | 128/1 |
| 4,402,307 | 9/1983 | Hanson et al. | 128/1 |
| 4,444,186 | 4/1984 | Wolvek et al. | 128/325 |
| 4,581,017 | 4/1986 | Sahota | 604/101 |
| 4,585,000 | 4/1986 | Hershenson | 128/345 |
| 4,597,755 | 7/1986 | Samson et al. | 604/96 |
| 4,646,719 | 3/1987 | Neuman et al. | 128/1 |
| 4,689,041 | 8/1987 | Corday et al. | 604/53 |
| 4,739,768 | 4/1988 | Engelson | 128/658 |
| 4,762,129 | 8/1988 | Bonzel | 128/344 |
| 4,771,777 | 9/1988 | Horzewski et al. | 128/344 |
| 4,787,388 | 11/1988 | Hofmann | 128/344 |
| 4,790,315 | 12/1988 | Mueller, Jr. et al. | 128/344 |
| 4,857,054 | 8/1989 | Helfer | 604/102 |
| 4,877,031 | 10/1989 | Conway et al. | 128/344 |
| 4,892,519 | 1/1990 | Songer et al. | 604/96 |
| 4,921,483 | 5/1990 | Wijay et al. | 604/96 |
| 4,944,745 | 7/1990 | Sogard et al. | 606/194 |
| 4,955,862 | 9/1990 | Sepetka | 604/164 |
| 4,976,720 | 12/1990 | Machold et al. | 606/194 |
| 4,981,478 | 1/1991 | Evard et al. | 604/282 |
| 4,983,167 | 1/1991 | Sahota | 606/194 |
| 4,998,917 | 3/1991 | Gaiser et al. | 604/96 |
| 4,998,923 | 3/1991 | Samson et al. | 606/194 |
| 5,000,734 | 3/1991 | Boussignac et al. | 604/96 |
| 5,046,503 | 9/1991 | Schneiderman | 128/692 |
| 5,061,273 | 10/1991 | Yock | 606/194 |
| 5,078,685 | 1/1992 | Colliver | 604/96 |
| 5,084,247 | 1/1992 | Horn et al. | 604/98 |
| 5,090,958 | 2/1992 | Sahota | 604/98 |
| 5,137,513 | 8/1992 | McInnes et al. | 604/96 |
| 5,147,377 | 9/1992 | Sahota | 606/194 |
| 5,158,540 | 10/1992 | Wijay et al. | 604/43 |

(List continued on next page.)

FOREIGN PATENT DOCUMENTS

| | | |
|---|---|---|
| 1289838 | 1/1988 | Canada . |
| 2014881 | 10/1990 | Canada . |
| 2045938 | 1/1992 | Canada . |
| 0 246 998 A2 | 11/1987 | European Pat. Off. . |
| 0 277 367 A1 | 8/1988 | European Pat. Off. . |
| 0 353 889 A1 | 2/1990 | European Pat. Off. . |
| 0 378 178 A2 | 7/1990 | European Pat. Off. . |
| 0 441 384 A2 | 8/1991 | European Pat. Off. . |
| 0 464 714 A1 | 1/1992 | European Pat. Off. . |
| 0 517 654 A2 | 12/1992 | European Pat. Off. . |
| 0 629 417 A2 | 12/1994 | European Pat. Off. . |
| WO 92/20398 | 11/1992 | WIPO . |
| WO 93/01856 | 2/1993 | WIPO . |
| WO 96/34580 | 11/1996 | WIPO . |

*Primary Examiner*—John D. Yasko
*Attorney, Agent, or Firm*—Crompton, Seager & Tufte, LLC

[57] ABSTRACT

Catheter for use in catheter procedures. The catheter includes a balloon carried at the distal end of an elongate shaft. A mechanism is included for providing a generally open perfusion passage while the balloon is in an inflated state. The perfusion passage provides both branch and distal perfusion. A mechanism is secured against the balloon for supporting the perfusion passage while the balloon is in an inflated state, and a mechanism is provided for retaining the balloon shape under pressure.

16 Claims, 7 Drawing Sheets

U.S. PATENT DOCUMENTS

| | | | |
|---|---|---|---|
| 5,160,321 | 11/1992 | Sahota | 604/96 |
| 5,195,971 | 3/1993 | Sirhan | 604/96 |
| 5,201,723 | 4/1993 | Quinn | 604/264 |
| 5,209,729 | 5/1993 | Hofmann et al. | 604/96 |
| 5,250,069 | 10/1993 | Nobuyoshi et al. | 606/192 |
| 5,279,562 | 1/1994 | Sirhan et al. | 604/96 |
| 5,284,473 | 2/1994 | Calabria | 604/53 |
| 5,295,961 | 3/1994 | Niederhauser et al. | 604/96 |
| 5,295,962 | 3/1994 | Crocker et al. | 604/101 |
| 5,300,025 | 4/1994 | Wantink | 604/96 |
| 5,300,085 | 4/1994 | Yock | 606/191 |
| 5,334,154 | 8/1994 | Samson et al. | 604/102 |
| 5,342,386 | 8/1994 | Trotta | 606/194 |
| 5,344,402 | 9/1994 | Crocker | 604/96 |
| 5,356,388 | 10/1994 | Sepetka et al. | 604/164 |
| 5,368,566 | 11/1994 | Crocker | 604/101 |
| 5,370,617 | 12/1994 | Sahota | 604/102 |
| 5,378,237 | 1/1995 | Boussignac et al. | 604/96 |
| 5,383,890 | 1/1995 | Miraki et al. | 606/194 |
| 5,395,332 | 3/1995 | Ressemann et al. | 604/96 |
| 5,395,333 | 3/1995 | Brill | 604/101 |
| 5,413,581 | 5/1995 | Goy | 606/194 |
| 5,425,711 | 6/1995 | Ressemann et al. | 604/96 |
| 5,433,706 | 7/1995 | Abiuso | 606/96 |
| 5,462,529 | 10/1995 | Simpson et al. | 604/101 |
| 5,556,382 | 9/1996 | Adams | 604/96 |
| 5,720,723 | 2/1998 | Adams | 604/96 |
| 5,749,825 | 5/1998 | Fischell et al. | 600/3 |
| 5,749,890 | 5/1998 | Shaknovich | 606/198 |
| 5,755,734 | 5/1998 | Richter et al. | 606/194 |
| 5,755,735 | 5/1998 | Richter et al. | 606/194 |
| 5,755,770 | 5/1998 | Ravenscroft | 623/1 |
| 5,755,771 | 5/1998 | Penn et al. | 623/1 |
| 5,755,772 | 5/1998 | Evans et al. | 623/1 |
| 5,755,773 | 5/1998 | Evans et al. | 623/1 |
| 5,755,778 | 5/1998 | Kleshinski | 623/1 |
| 5,776,101 | 7/1998 | Goy | 604/104 |
| 5,795,331 | 8/1998 | Cragg et al. | 604/96 |
| B1 4,762,129 | 7/1991 | Bonzel | 606/194 |

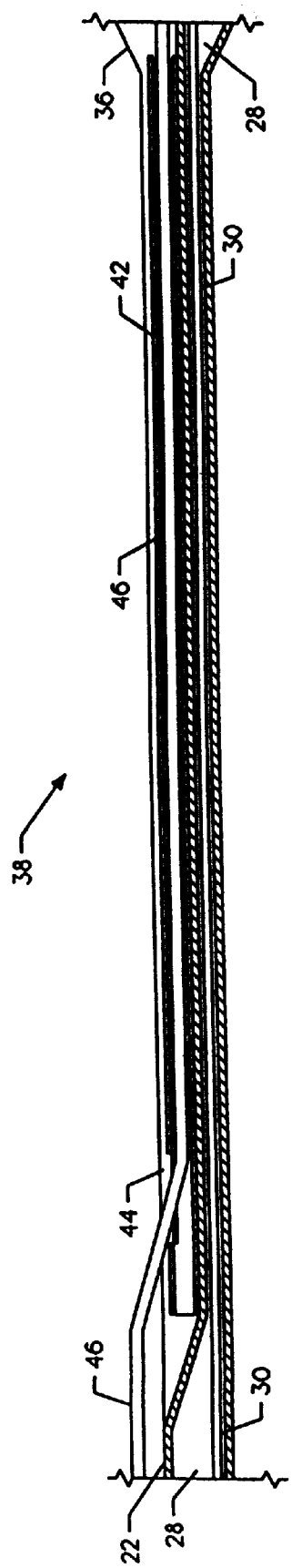

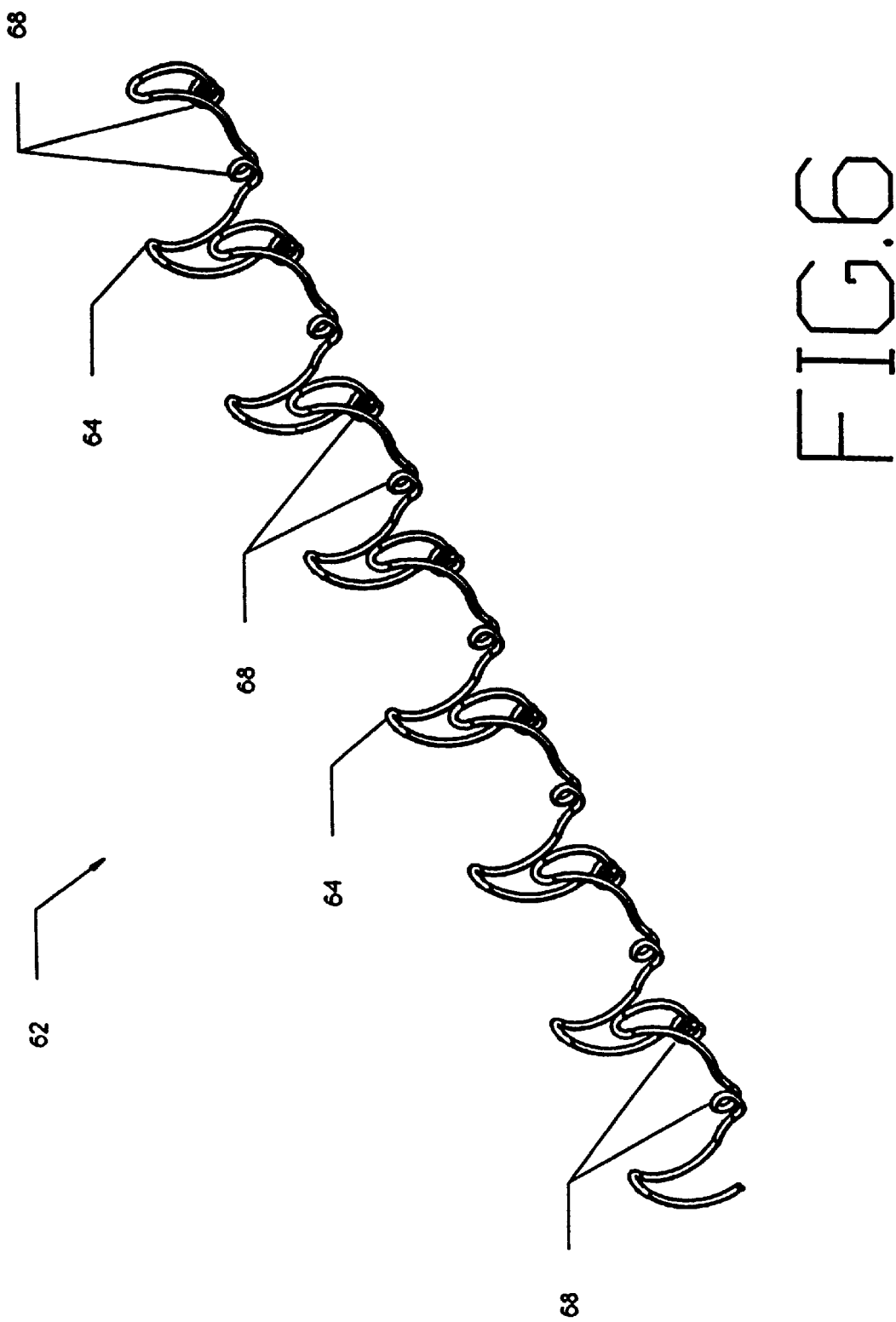

BALLOON PERFUSION CATHETER

This application is a continuation of application Ser. No. 08/636,246, filed Apr. 23, 1996, now U.S. Pat. No. 5,720,723 which in turn is a continuation of application Ser. No. 08/520,755, filed Aug. 29, 1995, now U.S. Pat. No. 5,556,382.

BACKGROUND OF THE INVENTION

The present invention relates to the field of angioplasty. In particular, the present invention relates to an intravascular perfusion catheter. The perfusion catheter is a dilatation balloon catheter, which provides both distal and side branch perfusion, and may be used for rapid exchange procedures.

Angioplasty procedures have gained wide acceptance in recent years as an efficient and effective method for treating certain types of vascular diseases. In particular, angioplasty is widely used for treatment of stenosis in the coronary arteries, although it is also used for treatment of stenosis in other parts of the vascular system.

The most widely used form of angioplasty makes use of a dilatation balloon catheter to treat a stenosis, and thereby reestablish an acceptable blood flow through the artery. The dilatation catheter includes an elongated tubular shaft and an inflatable balloon carried at a distal end of the shaft.

In operation, the catheter is inserted through a hollow guide catheter, which has been previously introduced into a patient's vascular system from a location remote from the heart (e.g., femoral artery). The proximal end of the guide catheter remains outside of the patient, while the distal end of the guide catheter is positioned at the ostium of the coronary artery to be dilatated.

A dilatation catheter is introduced into the proximal end of the guide catheter and advanced to the distal end of the guide catheter. Then, using fluoroscopy, the physician guides the dilatation catheter the remaining distance through the vascular system until the balloon is positioned across the stenosis therein. The balloon is inflated by supplying fluid under pressure through an inflation lumen in the catheter to the balloon.

The inflation of the balloon causes a widening of the lumen of the artery to reestablish acceptable blood flow through the artery. After a short inflation period, the balloon is deflated and the arterial treatment is evaluated to determine whether the procedure has reestablished an acceptable blood flow. If necessary, the dilatation procedure is repeated with the catheter balloon being reinflated.

Dilatation balloon catheters occlude blood flow while the balloon is expanded in the coronary artery. The balloon may be expanded for only a short inflation period, since occlusion of the coronary artery for extended periods may result in damage to portions of the heart which should receive blood from the occluded artery. Lack of blood circulation can lead to myocardial ischemia and angina, or anemic necrosis of tissues already stressed by the previously reduced level of blood flow.

One solution to allow extended inflation periods for complete treatment of the stenosis is the use of perfusion catheters. Perfusion catheters provide a path for blood to flow past the balloon, while the balloon is in an inflated state within the blood vessel. Thus, blood can be supplied to areas downstream of the inflated balloon during treatment of the stenosed artery.

U.S. Pat. No. 4,581,017 to Sahota suggests a perfusion catheter which includes a tubular shaft having a guide wire and perfusion lumen, and an inflation lumen. A dilatation balloon which communicates with the inflation lumen is carried at the distal end of the shaft. The tubular shaft includes at least one opening on the proximal side of the balloon and at least one opening on the distal side of the balloon, which communicate with the guide wire and perfusion lumen. When the balloon is inflated, blood may flow past the balloon by flowing through the proximal opening, through the guide wire and perfusion lumen, and out the distal opening.

Other perfusion catheters include a separate conduit for allowing blood to flow past the inflated balloon, such as is suggested in U.S. Pat. Nos. 4,983,167 and 5,147,377 to Sahota, U.S. Pat. No. 5,078,685 to Colliver, and U.S. Pat. No. 5,383,890 to Miraki et al. The perfusion conduits extend either through the dilatation balloon or along the outside of the dilatation balloon.

It is desirable to provide a dilatation balloon catheter which allows relatively high volumes of blood to flow past the balloon to a location distal of the balloon while the balloon is in an inflated state. Additionally, it is desirable to provide a perfusion catheter which allows blood flow to both distal and branch arteries. It is also desirable to provide a perfusion catheter which is low profile, and may be used in rapid exchange procedures.

SUMMARY OF THE INVENTION

The present invention is a perfusion balloon catheter for use in catheter procedures. In particular, the present invention includes a perfusion balloon catheter which provides both side branch and distal perfusion while the balloon is in an inflated state.

In one preferred embodiment, the present invention is a balloon perfusion catheter including an elongate shaft having a proximal end and a distal end, and an inflation lumen extending from the proximal end to the distal end. A balloon is carried by the shaft at the distal end. The balloon is in fluid communication with the inflation lumen. A structure is included for providing a generally open perfusion passage while the balloon is in an inflated state.

The structure for providing a generally open perfusion passage may include a support member secured against the balloon for supporting the passage while the balloon is in an inflated state. In alternative embodiments, the support member may be generally C-shaped, U-shaped, serpentine shaped, or coil shaped.

The perfusion passage may be located exterior to the balloon. Additionally, a retaining member may be included for retaining the balloon shape under pressure. The retaining member may include a perfusion wrap secured around the balloon. The perfusion wrap allows side branch perfusion. In one embodiment, the perfusion wrap is formed of strands. In another embodiment, the wrap includes a thin sleeve having side holes for side branch perfusion.

In yet another embodiment, the present invention includes a catheter for use in catheter procedures. The catheter includes an elongate shaft having a proximal end and a distal end and an inflation lumen extending therethrough. A balloon is carried by the shaft at the distal end. The balloon is in fluid communication with the inflation lumen. A mechanism is included for providing a generally open perfusion passage while the balloon is in an inflated state, including a perfusion wrap for retaining the shape of the balloon when the balloon is in an inflated state.

The perfusion passage may provide both side branch and distal perfusion. The perfusion passage may further include a guide wire passage.

Additionally, the mechanism for providing a generally open perfusion passage may include a generally open support member carried adjacent the balloon for supporting the passage while the balloon is in an inflated state. The support member may include the means for slidably retaining a guide wire.

In yet another embodiment, the present invention includes a method of providing a perfusion passage during a catheter procedure. A shaft is provided having a balloon carried at a distal end, including an inflation lumen extending therethrough in communication with the balloon. The balloon is inflated within an artery. Blood flows past the balloon through a perfusion passage to side and distal branches while the balloon is in an inflated state. A generally open support member is included which is carried by the balloon.

The shape of the balloon is retained with a balloon wrap during inflation of the balloon. The balloon wrap may be formed of strands. Additionally, a guide wire may be passed through the perfusion passage. The guide wire may be passed through the support member. In one embodiment, the support member is of a generally serpentine shape.

The balloon catheter of the present invention provides a perfusion passage allowing both distal and branch perfusion during inflation of the catheter balloon. The balloon catheter of the present invention allows large amounts of blood to pass through the perfusion passage. Additionally, the present invention maintains the shape of the balloon during inflation of the balloon.

The present invention may be used in a low profile balloon catheter system for dilatating a stenosis. Additionally, a guide wire may be movably received through the perfusion passage for use in rapid exchange procedures, or for maintaining a path across the stenosis during catheter procedures.

BRIEF DESCRIPTION OF THE DRAWINGS

The invention will be further described with reference to accompanying drawings where like numbers refer to like parts throughout the several views, and wherein:

FIG. 2A is a longitudinal expanded cross-sectional view taken along line 2A—2A of FIG. 2;

FIG. 6 is a perspective view of a balloon support member in accordance with the present invention.

DETAILED DESCRIPTION OF THE PREFERRED EMBODIMENTS

Figure 1:
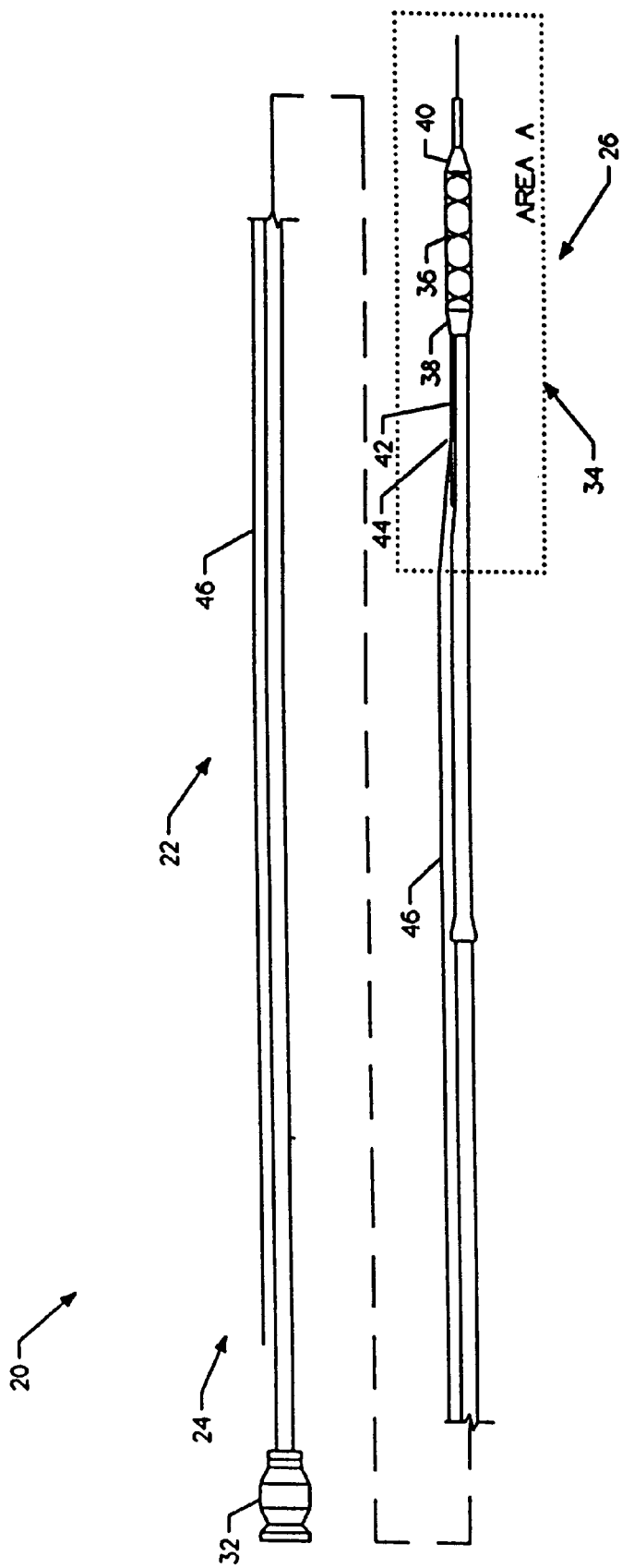
FIG. 1 is a perspective view of a catheter in accordance with the present invention.

FIG. 1 illustrates an intraluminal catheter of the present invention for use as an angioplasty dilatation balloon catheter generally at 20. The catheter 20 includes a shaft 22 having a proximal end 24 and a distal end 26. An inflation lumen 28 extends longitudinally through the shaft 22 from the proximal end 24 to the distal end 26 (shown in FIG. 3).

Operably connected to the proximal end 24 of the shaft 22 is a hub or luer assembly 32 which communicates with the inflation lumen 28. The luer assembly 32 provides for connection to other catheter devices, such as a Y adapter, during a catheterization procedure.

In one embodiment, shaft 22 can be similar to the shaft disclosed in U.S. Pat. No. 5,425,711 to Ressemann et al., which is herein incorporated by reference. In general, Ressemann et al. discloses a shaft formed from an elongated metallic tube having an inflatable balloon at its distal end. A plastic tube connects a distal end of the metallic tube to the proximal end of the balloon. The metallic and plastic tubes thus define a lumen for providing inflation pressure to the balloon. The metallic tube and core member provide the necessary pushability for the catheter to permit its highly controlled advancement along a guide wire, and for tracking the guide wire through tortious vascular lumens.

Figure 2:
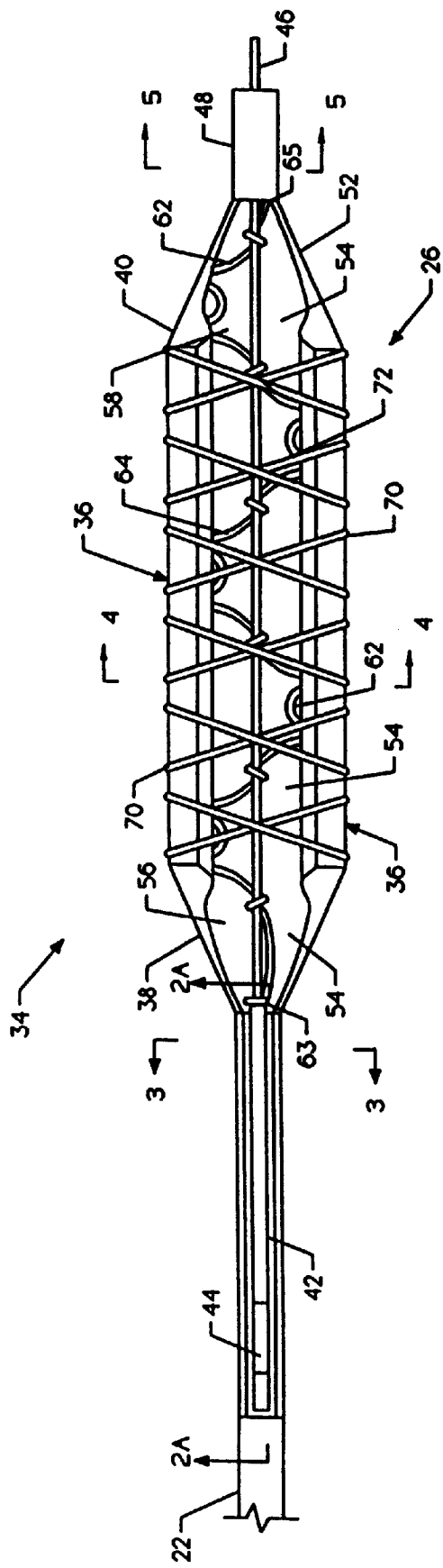
FIG. 2 is a top view of the catheter taken at area A of FIG. 1.

Referring to FIG. 2, which is an enlarged top view of area A shown in FIG. 1, the distal end 26 of the balloon catheter 20 is shown. Carried at a distal end of the shaft 22 is a dilatation balloon system 34 indicated within dashed area A. The dilatation balloon system 34 includes a dilatation balloon 36 having a proximal end 38 and a distal end 40. Referring to FIG. 2A, a cross-sectional side view of the proximal end 38 of the dilatation balloon system 34 is shown.

Located at the proximal end 38 of dilatation balloon 36 is guide wire conduit 42 having an opening 44. Guide wire conduit 42 is secured to shaft 22 and extends to the proximal end 38 of dilatation balloon 36. Guide wire 46 passes through guide wire conduit 42 for advancing the balloon catheter 20 over the guide wire 46. In one embodiment, the guide wire conduit 42 is formed of a stainless steel hypotube.

Figure 3:
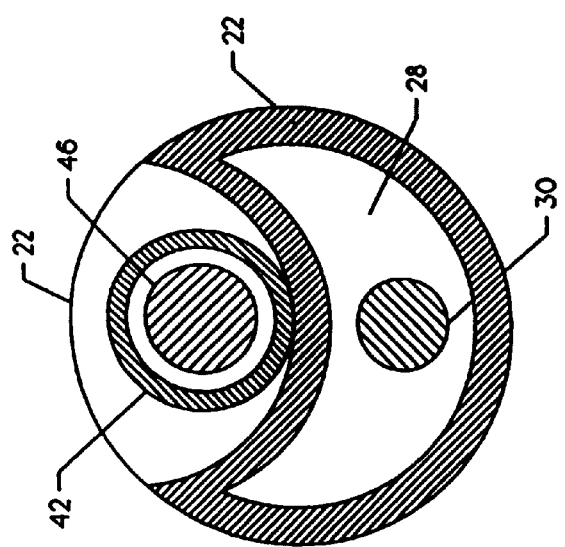
FIG. 3 is a cross-sectional view of the catheter taken along line 3—3 of FIG. 2.

Referring also to FIG. 3, which is a cross-sectional view of the proximal end 38, inflation lumen 28 is in fluid communication with dilatation balloon 36 for inflation of dilatation balloon 36 during an angioplasty procedure. Core member 30 extends through inflation lumen 28.

Figure 4:
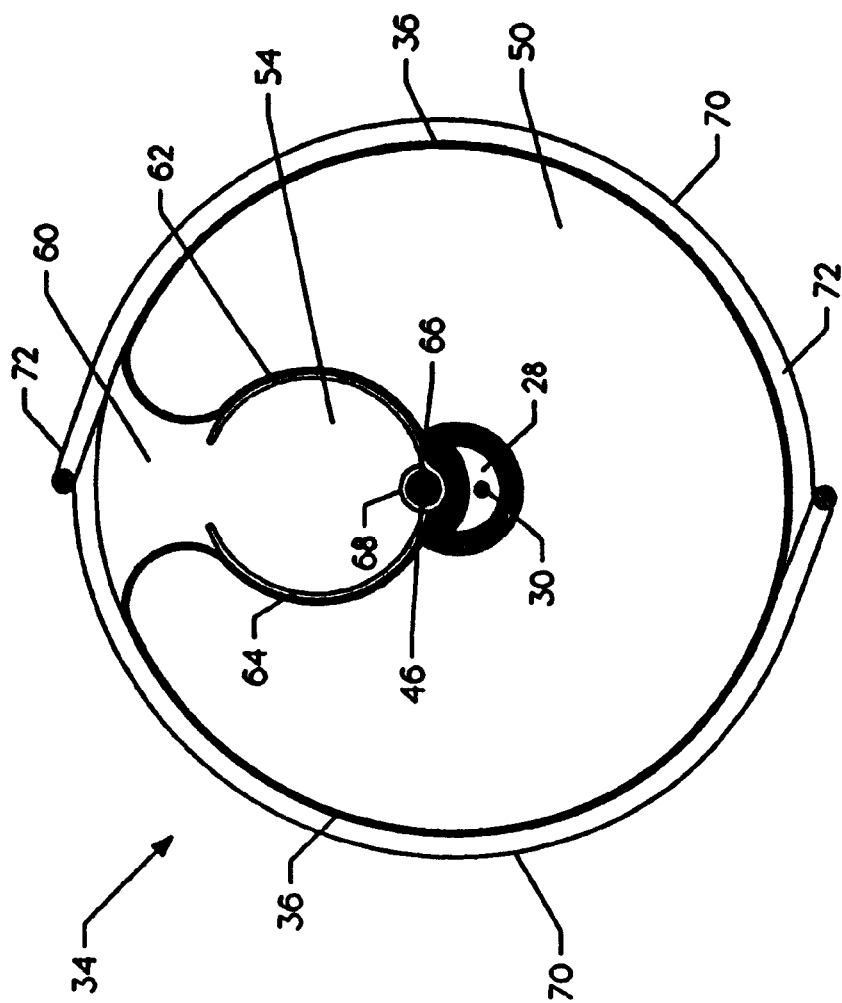
FIG. 4 is a cross-sectional view of the catheter taken along line 4—4 of FIG. 2.

Referring to FIG. 4, balloon 36 includes an interior 50 in fluid communication with the inflation lumen 28 of shaft 22. The balloon 36 is formed of suitable balloon material as known in the art. In one preferred embodiment, the suitable balloon material is a polyolefin which has been treated by electron beam cross linking. A suitable polyolefin is available from E.I. DuPont de Moores Company of Wilmington, Del. under the tradename SURLYN® (8527) Ionomer. Balloon 36 may also be coated with a lubricous material, such as a silicone or hydrophilic lubricant. Balloon length varies depending upon the desired size of the dilatation catheter, with typical balloon lengths 10 to 40 ml. A typical preferred dilatation diameter for the balloon is 1.5 to 4 mm.

Core member 30 extends through the balloon 36 interior 50 within inflation lumen 28. A distal neck 52 located at the distal end 40 is sealably connected to a distal member 48 by a suitable adhesive and sealing material such as LOCKTIGHT PRISM 405, a cyanoacrylate available from Locktight Corp. of Newington, Conn., or TRADEBOND 2315D, an epoxy available from Tra-Con, Inc. of Medford, Mass.

Core member 30 is secured to the distal end member 40 of dilatation balloon 36 at distal member 48. A radiopaque marker band may be located along core member 30, centered within dilatation balloon 36 to aid in positioning dilatation balloon 36 across the stenosis during the angioplasty procedure.

Figure 5:
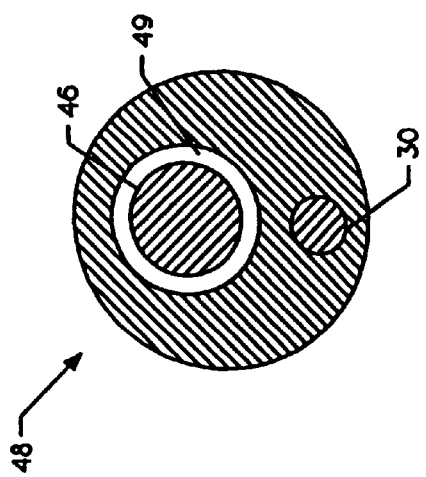
FIG. 5 is a cross-sectional view of the catheter taken along line 5—5 of FIG. 2.

Referring to FIG. 5, a cross section of the distal member 48 is shown. As previously stated, core member 30 terminates at distal member 48 and is secured to distal member 48 by an adhesive. Additionally, guide wire 46 extends through distal member 48 through an opening 49.

A perfusion passage 54 extends longitudinally along the exterior of dilatation balloon 36. The perfusion passage 54 allows a relatively large volume of blood to flow past an inflated balloon 36 for perfusion of both side branch and distal coronary arteries.

Perfusion passage 54 is defined by the exterior of balloon 36. Perfusion passage 54 includes proximal opening 56, distal opening 58, and branch opening 60 along the entire longitudinal length of balloon 36. A support member 62 is secured to the exterior 64 of balloon 36 for defining and maintaining the perfusion passage 54 during inflation of balloon 36.

Support member 62 is of a generally C-shaped or U-shaped cross section, having an opening toward branch opening 60 along the longitudinal length of dilation balloon 36. In one preferred embodiment, support member 62 is secured to the external balloon surface by a urethane. The proximal end of support member 62 encircles and is bonded to guide wire conduit 42, indicated at 63. The distal end of support member 62 is bonded to distal member 48, indicated at 65.

In one preferred embodiment shown in FIG. 6, support member 62 is generally serpentine shaped and formed of wire. The serpentine shaped wire 64 extends from the proximal opening 56 through the perfusion passage 54 to the distal opening 58. The generally serpentine shaped wire 64 is formed having a generally U-shaped or C-shaped bend in the middle corresponding to the desired cross section of the perfusion passage. Alternatively, it is recognized that the perfusion passage 54 support member 62 may take on other shapes within the scope of this invention, such as a spiral-shaped wire. Support member 62 is formed of a shape that is generally open, allowing both branch and distal perfusion through the perfusion passage 54.

The support member 62 provides support to the perfusion passage 54 during inflation of balloon 36 without undue rigidity that a tubular or conduit member has. As the balloon 36 is inflated, the support member 62 keeps balloon 36 from collapsing the perfusion passage 54.

Additionally, guide wire 46 can extend through perfusion passage 54. As shown in FIG. 6, the serpentine wire 64 includes loop members 68 for slidably retaining guide wire 46. In one preferred embodiment, the support member 62 is coated with a lubricous polymer for ease of movement of guide wire 46 relative to members 68.

A wrap 70 is located around balloon 36 to maintain the desired balloon shape during inflation of the balloon. Wrap 70 is a generally flexible member, which is secured to the balloon 36 exterior surface, and collapses with the balloon 36 when balloon 36 is in a deflated state. Although in one preferred embodiment, wrap 70 crosses the branch opening 60 of balloon 36, wrap 70 is generally open to allow branch perfusion.

In one preferred embodiment, wrap 70 is a balloon shape retainer formed of braided strands. The braided strands are preferably a high-strength polymer fiber, such as polyamide, polyester, or aramid. The strands 72 are secured to the balloon 36 exterior surface by coating the entire stranded wrap 70 with urethane or by using an adhesive such as epoxy at the balloon 36 proximal end 38 and distal end 40. Although the urethane may cover the entire wrap 70 strands 72, the urethane does not close the openings between the strands 72, nor otherwise interfere with side branch perfusion.

In an alternative embodiment, the wrap 70 includes strands 72 which are spiral wrapped around the balloon, the spiral wrap extending from the balloon proximal end 38 to the balloon distal end 40. The strands 72 are secured to the balloon 36 using an adhesive at the proximal end 38 and the distal end 40. In one preferred embodiment, the adhesive is a urethane adhesive.

Figure 7:
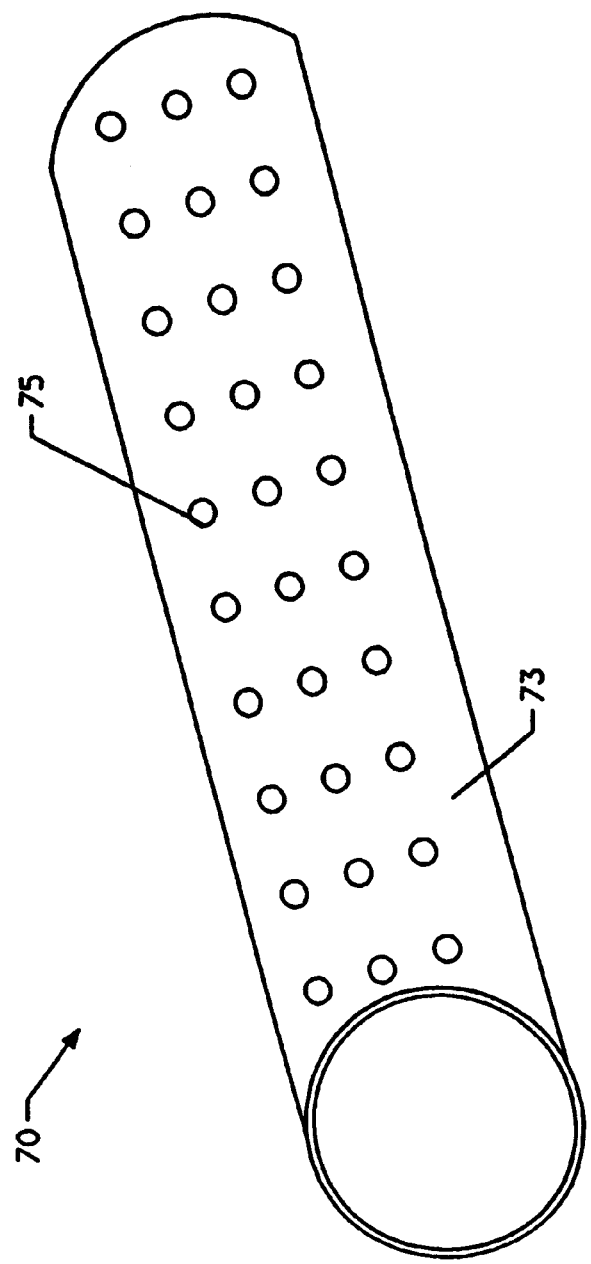
FIG. 7 is a perspective view of a balloon wrap in accordance with the present invention.

Referring to FIG. 7, an alternative embodiment of wrap 70 is shown. Wrap 70 includes a relatively thin sleeve 73 having openings 75. Sleeve 73 is formed of a polymeric material. In one preferred embodiment, sleeve 73 is secured to balloon 36 by heat bonding the sleeve 73 to the balloon 36. Openings 75 allow side branch perfusion of blood.

As balloon 36 is inflated, wrap 70 flexes with the inflated balloon 36 retaining the shape of balloon 36 as the balloon forms the perfusion passage 54 defined by support member 62. Since wrap 70 is generally open, wrap 70 does not interfere with side branch perfusion. Additionally, as balloon 76 is deflated, wrap 70 is flexible and recedes from its inflated shape retaining position.

Guide wire 46 extends through guide wire conduit 42, perfusion passage 54, and distal member 48 allowing the position of guide wire 46 to be maintained across the stenosed region during positioning and removal of catheter 20. Additionally, the passage of guide wire 46 extends through the distal end 26 of balloon catheter 20 allowing balloon catheter 20 to be used for rapid exchange procedures.

In a typical coronary angioplasty procedure, the femoral artery is entered percutaneously and a sheath is inserted into the artery to provide access to the patient's vascular system. A guide catheter (not shown) is introduced over a guide wire through the previously placed femoral introducer sheath and advanced up to the aortic arch. The guide catheter is advanced and maneuvered until a distal end thereof is properly engaged in the ostium of the coronary artery to be dilatated. A Y adapter manifold assembly may be attached to the guide catheter hub at the proximal end for implementation of therapeutic procedures, such as dye delivery, flushing capabilities, pressure monitoring, and delivery of the dilatation balloon system.

Once the guide catheter is in place, the guide wire 46 is then aligned in the stenosed artery to a desired position through the stenosis. The angioplasty dilatation balloon catheter 20 of the present invention is advanced along the guide wire 46 to position the balloon across the stenosis.

During inflation of the balloon for treatment of the stenosed artery, blood flow is occluded within the artery. Occlusion of a coronary artery cannot be permitted for more than a limited time without incurring risk of damage to portions of the vascular system which receive blood from the occluded artery. Even relatively short balloon inflation periods give rise to a risk of myocardial ischemia or necrosis of the downstream tissues stressed by the reduced level of blood flow. Therefore, the balloon 36 is inflated for relatively short periods of time and then deflated to restore circulation through the artery being treated.

The balloon catheter 20 of the present invention is a perfusion catheter which allows blood to flow through the balloon during the period of time that the balloon is in an inflated state. The dilatation balloon 36 has a perfusion passage which allows a large volume of blood to flow to both branch and distal arterial regions during balloon inflation and treatment of the stenosis. During the angioplasty procedure, the physician may need to rotate the balloon to align the side branch perfusion region with the desired side branch. The perfusion passage allows treatment of the stenosed artery for extended periods of time, limiting the serious risk of myocardial ischemia and anemic necrosis of tissues stressed by the reduced level of blood flow and other damage to portions of the heart which should receive blood from the artery receiving treatment.

Additionally, the perfusion catheter of the present invention is a low profile catheter which allows treatment of stenosed arteries in distal regions of the patient's vascular system. The guide wire extends through the perfusion passage for allowing the guide wire to be maintained across the stenosed area during catheter exchange procedures.

It will be understood that this disclosure is, in many respects, only illustrative. Changes may be made in details, particularly in matters of shape, size, material, and arrangement of parts, without exceeding the scope of the invention. Accordingly, the scope of the invention is as defined in the language of the appended claims.

What is claimed is:

1. A balloon catheter, comprising:

an elongate shaft having a proximal end and a distal end, and defining an inflation lumen therethrough;

a balloon connected to the shaft at the distal end; and a guidewire tube disposed proximate and externally of the distal end of the shaft, the tube having a proximal end and a distal end, the distal end being disposed proximally of the distal end of the balloon, and wherein the shaft at least partially surrounds the guidewire tube.

2. The catheter of claim 1, wherein the passage has a maximum width that is greater than the width of the side opening.

3. The catheter of claim 1, wherein the passage is located adjacent the inflation lumen.

4. The catheter of claim 3, wherein the inflation lumen is located along a longitudinal center axis of the balloon.

5. The catheter of claim 1, further comprising a support member positioned within the passage for supporting the passage during inflation of the balloon.

6. The catheter of claim 5, wherein the support member generally includes a proximal opening, a distal opening, and a side opening.

7. The catheter of claim 6, wherein the maximum width of the support member is greater than the width of the side opening.

8. The catheter of claim 6, wherein the support member is a generally tubular shaped member.

9. The catheter of claim 1, further including a shape retaining member for retaining the shape of the balloon when it is in an inflated state.

10. The catheter of claim 9, wherein the shape retaining member allows fluid to pass therethrough.

11. The catheter of claim 9, wherein the shape retaining member includes a support member positioned within the passage for supporting the passage during inflation of the balloon.

12. The catheter of claim 1, wherein the passage is formed by the exterior of the balloon.

13. A method of providing access to a vessel side branch from a location proximal of an inflated balloon, comprising the steps of:

providing a balloon catheter including a shaft having a proximal end and a distal end, and a balloon assembly disposed proximate the distal end of the shaft, the balloon assembly having a proximal end, a distal end and a side;

defining a passage extending distally into the balloon assembly such that the passage has a first opening proximate the proximal end of the balloon and a more distally disposed second opening at the side of the balloon assembly; and disposing the balloon assembly in a vessel such that the balloon assembly is disposed adjacent a side branch vessel opening such that the second opening is adjacent the side branch vessel opening.

14. The method in accordance with claim 13, further comprising the steps of providing a generally cylindrical, expandable metallic member, and disposing the cylindrical member around the balloon assembly.

15. The method in accordance with claim 14, further comprising the steps of providing a second generally cylindrical metallic member, and placing the second generally cylindrical member around the guidewire and within the passage.

16. The method in accordance with claim 13, further comprising the steps of providing a guidewire, and placing the guidewire into the passage.

* * * * *